(12) United States Patent
Pham

(10) Patent No.: US 8,501,645 B2
(45) Date of Patent: Aug. 6, 2013

(54) ENHANCED FILAMENTOUS SILICONE PRODUCTS AND PROCESSES

(75) Inventor: Van Hai Pham, Irvine, CA (US)

(73) Assignee: Donna K. Jackson, Fort Worth, TX (US)

( * ) Notice: Subject to any disclaimer, the term of this patent is extended or adjusted under 35 U.S.C. 154(b) by 1417 days.

(21) Appl. No.: 11/171,900

(22) Filed: Jun. 30, 2005

(65) Prior Publication Data

US 2007/0003759 A1   Jan. 4, 2007

(51) Int. Cl.
*D02G 3/22* (2006.01)

(52) U.S. Cl.
USPC ......... 442/339; 428/304.4; 428/376; 428/397

(58) Field of Classification Search
USPC ..................... 428/376, 397, 304.4; 442/339
See application file for complete search history.

(56) References Cited

U.S. PATENT DOCUMENTS

| | | | |
|---|---|---|---|
| 4,753,978 A | 6/1988 | Jensen | |
| 5,176,708 A | 1/1993 | Frey et al. | |
| 5,779,734 A | 7/1998 | Ledergerber | |
| 5,961,552 A * | 10/1999 | Iversen et al. | 623/8 |
| 6,030,416 A | 2/2000 | Huo et al. | |
| 6,371,984 B1 | 4/2002 | Van Dyke et al. | |
| 6,465,010 B1 | 10/2002 | Lagoviyer et al. | |
| 6,511,508 B1 | 1/2003 | Shahinpoor et al. | |
| 6,585,504 B2 | 7/2003 | Weiss | |
| 6,612,823 B2 | 9/2003 | Bandou et al. | |
| 6,722,869 B2 | 4/2004 | Todokoro | |
| 6,767,551 B2 | 7/2004 | McGhee et al. | |
| 2007/0185575 A1 | 8/2007 | Purkait | |
| 2008/0280207 A1 | 11/2008 | Patoux et al. | |

FOREIGN PATENT DOCUMENTS

| | | |
|---|---|---|
| EP | 748848 A2 * | 12/1996 |
| EP | 1895032 A2 | 3/2008 |
| JP | 53016747 A | 2/1978 |
| JP | 63046230 A | 4/1986 |
| JP | 62133163 A * | 6/1987 |
| JP | 62161513 A | 7/1987 |
| KR | 10-1999-0001782 | 1/1999 |
| WO | WO 03/026537 A1 | 4/2003 |

OTHER PUBLICATIONS

Lederman and Klatzky (1987) Cognitive Psychology. 19:342-368.
Silastic® Q7 4850 Part A, Nov. 5, 2009.
Silastic® Q7 4850 Part B , Jun. 11, 2010.
International Search Report. Jun. 29, 2012.

* cited by examiner

*Primary Examiner* — Elizabeth Cole
(74) *Attorney, Agent, or Firm* — Peter Jon Gluck; Greenberg Traurig

(57) ABSTRACT

Filamentous bodies which are longitudinally extended and other film-like constructions are made by combining liquid silicone-containing precursors with air and extruding them. Distinct types or grades of fibers, strands, and other film-like constructions are produced which have a multiplicity of useful applications and indications for use owing to their inherent memory, compactability, tensile strength and density. Processes for making the novel enhanced filamentous bodies and products by the same can be optimized for uses ranging from safe and effective ("leak-free") prosthetics to cushions, inserts, membranes, in a plurality of fields from consumer electronics to medical devices, and athletic or orthopedic shoe inserts.

5 Claims, 10 Drawing Sheets

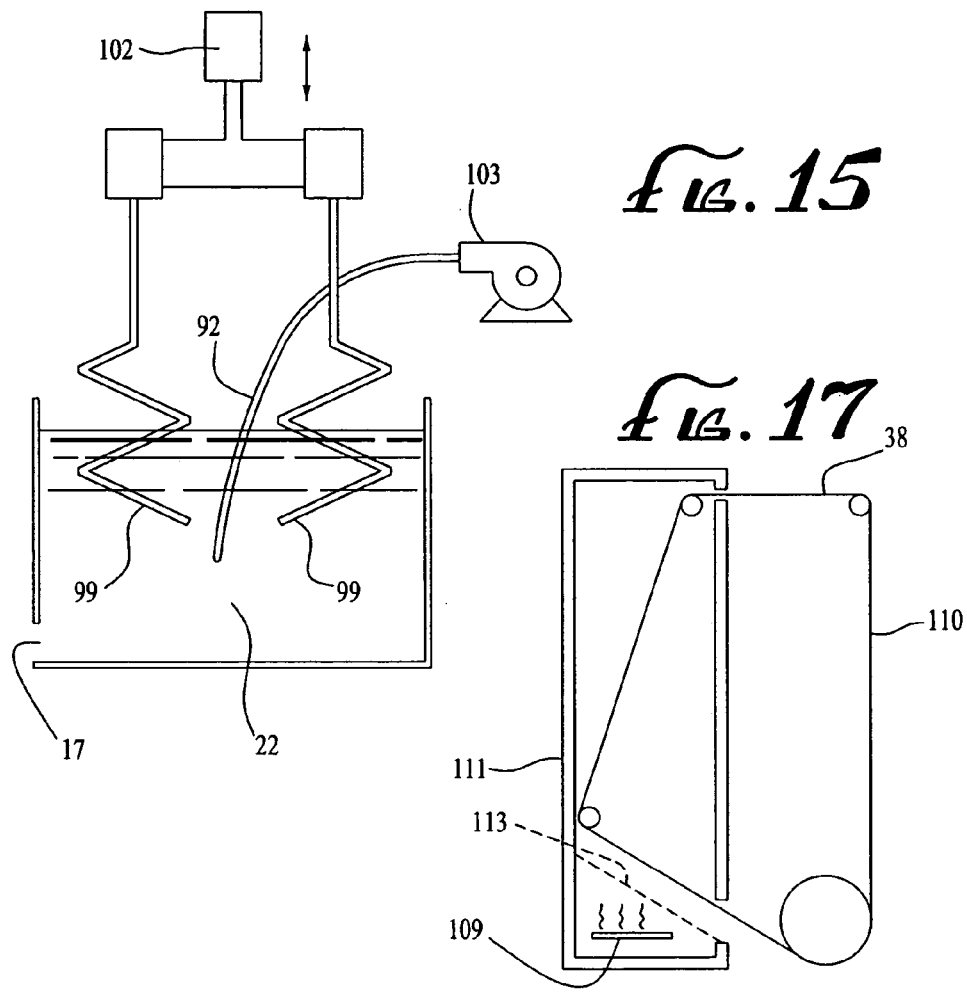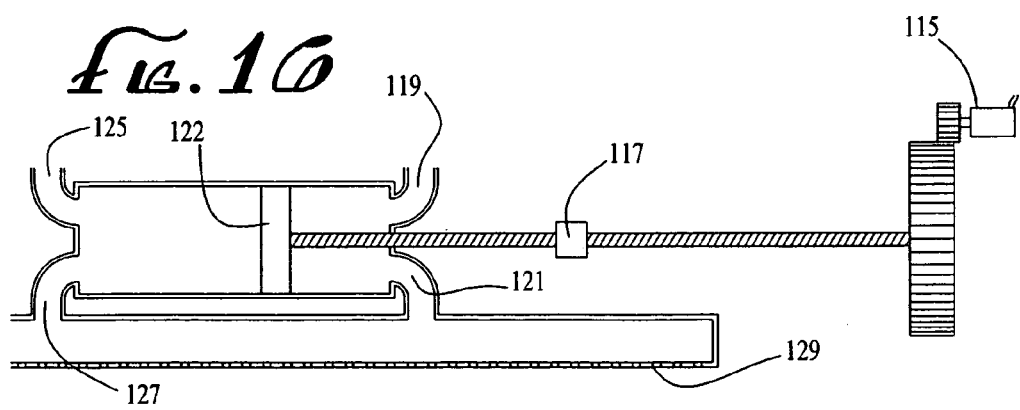

 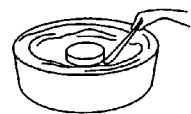 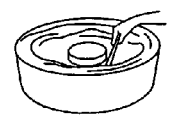
FIG. 18A  FIG. 18B  FIG. 18C
  
FIG. 18D  FIG. 18E  FIG. 18F
 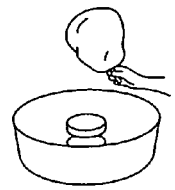
FIG. 18G  FIG. 18H

ENHANCED FILAMENTOUS SILICONE PRODUCTS AND PROCESSES

BACKGROUND OF THE DISCLOSURE

The present disclosure relates to novel silicone-based products and fabrication processes. In particular, the present disclosure relates to silicone-based products heretofore unavailable, in the form of fibers, strands, threads, and other filamentous bodies, or by products made by further processing the same, and methods for generation of these novel products.

DESCRIPTION OF THE PRIOR ART

While thousands of finished silicone-based products are known, it is respectfully proposed that prior to the advent of the instant teachings longstanding needs remain. For example, prosthetic implants such as that discussed in U.S. Pat. No. 5,176,708 have been plagued by longstanding issues, and have not been improved in spite of tremendous demands in the marketplace. Many have been harmed by these products, particularly silicone breast implants which have leaked. Those skilled in the art understand the primary pitfalls in the area, so further details of these failures themselves are omitted from this discussion, which, it is respectfully proposed, focuses upon the teachings of the present disclosure which are believed to be a paradigm shifting improvement applicable to this field of art.

Likewise, fillers, such as those described in U.S. Pat. No. 6,013,234 and U.S. Pat. No. 3,383,172 have long been sought for many needs, yet fraught with issues of their own. Significant among these shortcomings are price, ease of manufacturability, consistency and general ability to be used for alternative types of applications. The search for substantially weightless, robustly tensile and memory-laden silicone constructions is ongoing.

Compositions of silicone-related materials and ways of making them ranging from U.S. Pat. No. 4,094,771 to U.S. Pat. No. 4,753,978 have long been sought to fill particular industrial needs. Each of the foregoing Letters Patent documents is herein expressly incorporated by reference as if fully set forth in this specification, yet none has pointed toward the teachings of the present disclosure, short of underscoring the clear needs for the objects of the teachings of the instant disclosure.

The teachings of the present disclosure have produced a new silicone end product different from those silicones known, industrially or commercially used or contemplated to date.

SUMMARY OF THE DISCLOSURE

Briefly stated filamentous bodies which are longitudinally extended and other film-like constructions are made by combining liquid siliceous precursors with air and extruding them. Distinct types or grades of fibers, strands, and other film-like constructions are produced which have a multiplicity of useful applications and indications for use owing to their inherent memory, compactability, tensile strength and density. Processes for making the novel enhanced filamentous bodies and products by the same can be optimized for uses ranging from safe and effective ("leak-free") prosthetics to cushions, inserts, membranes, in a plurality of fields from consumer electronics to medical devices, and athletic or orthopedic shoe inserts.

According to features of the present disclosure there are provided novel aerated silicone filaments defined by a visible longitudinally extended axis having elastic memory, tensile strength and a sufficiently high fill density in a compacted state rendering them effective for occupying a predetermined space over time without measurable compression within that space.

According to further features of the present disclosure there are provided novel enhanced prosthetic devices which comprise, in combination, at least a flexible container for receiving a plurality of filamentous silicone members, and a plurality of filamentous silicone members housed with the container.

Yet still another feature of the present disclosure defines silicone filaments by a visible longitudinally extended axis having a central plane defined by a cathetus and elastic memory, tensile strength and a sufficiently high fill density in a compacted state rendering them effective for occupying a predetermined space over time without measurable compression within that space. Novel aerated silicone filaments defined by having a nano scale longitudinally extended axis having a central plane defined by a cathetus and elastic memory, tensile strength and a sufficiently high fill density in a compacted state rendering them effective for occupying a predetermined space over time without measurable compression within that space.

An additional feature of the present disclosure provides aerated silicone filaments defined by having a pico scale longitudinally extended axis having a central plane defined by a cathetus and elastic memory, tensile strength and a sufficiently high fill density in a compacted state rendering them effective for occupying a predetermined space over time without measurable compression within that space.

Yet a still further feature of the present disclosure provides novel aerated silicone filaments defined by having a meso scale longitudinally extended axis having a central plane defined by a cathetus and elastic memory, tensile strength and a sufficiently high fill density in a compacted state rendering them effective for occupying a predetermined space over time without measurable compression within that space.

Likewise, still yet another further feature of the present invention is an aerated silicone filament defined by having a micron scale longitudinally extended axis having a central plane defined by a cathetus and elastic memory, tensile strength and a sufficiently high fill density in a compacted state rendering it effective for occupying a predetermined space over time without measurable compression within that space.

Similarly, the present invention features a novel aerated silicone filament defined by having a millimeter scale longitudinally extended axis having a central plane defined by a cathetus and elastic memory, tensile strength and a sufficiently high fill density in a compacted state rendering them in groups to be effective for occupying a predetermined space over time without measurable compression within that space.

Yet still another further feature of the present invention provides novel aerated silicone filaments defined by having a centimeter scale longitudinally extended axis having a central plane defined by a cathetus and elastic memory, tensile strength and a sufficiently high fill density in a compacted state rendering them effective for occupying a predetermined space over time without measurable compression within that space.

Likewise features of the present disclosure are directed toward processes for making and using the teachings of the present disclosure and toward fabricating versions, species and sub-species which are directed toward specific applications. For example, there is provided a process for generating filamentous strands of silicone, comprising, in combination, the steps of providing aliquots of two different silicone precursors, combining at least one of the ratios selected from the group consisting of 30/70, 40/60 and substantially equal aliquots of the two different liquid silicone precursors, adding air to the combinant silicone mixture, mixing the resulting silicone emulsion to create a fluffed emulsion, pressing the fluffed emulsion through a pressing machine equipped with a die plate, extruding silicone filaments onto a dish, and drying the silicone filaments inside of a heating chamber. Products by this and the related processes detailed in the instant specification are likewise taught.

BRIEF DESCRIPTION OF THE FIGURES

The above-mentioned features and objects of the present disclosure will become more apparent with reference to the following description taken in conjunction with the accompanying drawings wherein like reference numerals denote like elements and in which:

FIG. 15 shows an assembly used according to a process for making the instant disclosure;

FIG. 16 shows an assembly used according to an alternate process for making the instant disclosure;

FIG. 17 shows an assembly used according to an alternate process for making the instant disclosure;

FIG. 18 A through H each shows one step in an alternate process used according to the method for making the instant disclosure;

DETAILED DESCRIPTION OF THE DISCLOSURE

The present inventor has discovered novel enhanced filamentous silicone strands, fibers, threads, and film-like constructions can be easily generated which have a multiplicity of useful applications. Heretofore uncontemplated, the products of the present disclosure allow for various usages that address, ameliorate and otherwise overcome longstanding needs, such as in the silicone prosthetic implant field, which filed is rife with issues currently. Other uses will become known to artisans in perusing the instant specification and studying the claims which are appended hereto.

Example 1

Figure 1:
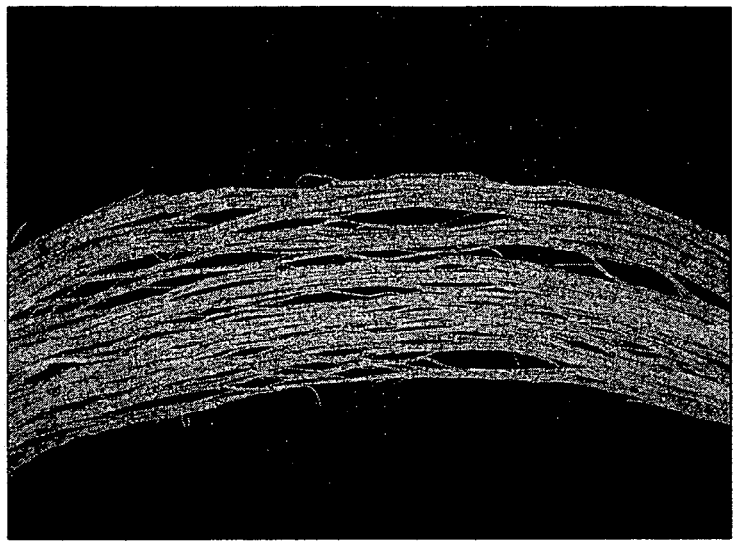
FIG. 1 shows a photograph of an embodiment of novel silicone filaments according to the teachings of the present disclosure.

Referring now to FIG. 1 silicone filament is shown which may be created from a combination of conventional silicone precursor elements as known to those skilled in the art from liquid silicone rubber parts A (catalyst: reinforced dimethyl methylvinyl siloxanes), Part B (crosslinking agent: reinforced dimethyl methylhydrogen) (For example, Rhodia-A LSR-4330 Silbione® HCA Part #V50131A-40 Lot 0409031, B LSR-10 Silbione® HC Part #V500004B-40 Lot 26776, Medical Grade available from Rhodia Europe/Rhodia SA, 26, quai Alphonse Le Gallo, 92512 Boulogne-Billancourt cedex and Rhodia Amerique du Nord/Rhodia Inc., 259 Prospect Plains Road, CN 7500, Cranbruy N.J. 08512-7500) which is then whipped, beaten and extruded through a die according to the teachings of the present disclosure. Likewise heat cured silicone rubbers are commercially available in 2 parts systems (A and B). These parts need to be precisely mixed to produce consistent product, requiring controlled pumping and mixing equipment. In 2004 Laur Silicone developed a ONE PART™ heat curable liquid silicone rubber using the EASY CURE™ technology (patent pending). This EASY CURE™ system greatly reduces the requirements for meter mix equipment. ONE PART™ liquid silicone can be supplied fully compounded and ready to use.

According to the teachings of the present disclosure, the aerated or fluffed emulsion cures, encapsulating gaseous elements which create heretofore unconstructed silicone products having many uses.

Extruding nozzles or screen assemblies and die plates may alternately be employed having aperture configurations which drive aspects of the specific tubular orientation desired to be achieved. Artisans understand that liquid silicone materials will not be altered in terms of physical properties until adequate temperatures are achieved, for example (once A and B are mixed, these materials have short pot lives that are inversely related to temperature) and the instant disclosure has used a heating chamber at 350 degrees Fahrenheit which circulates hot air to house the extrudate for drying.

Fabricators typically operate at vulcanization temperatures between 250° and 375° F. Actual results will depend on the design and size. According to this example, as the elongated filaments are extruded through the apertures or screen elements long strands hang curtain-like downward.

The curtain-like strands or threads, filaments, fibers, twines may be extruded directly from the die plate into the drying chamber, for example, the curtain-like group of filaments is deposited directly on a metal mesh that prevents sticking and allows for easy removal. The metal mesh itself is mounted on a moving belt that pushes the filaments outside of the heating chamber for easy removal, where they are reeled on a cocoon-like holding rod. A resulting product has diameter that varies between a few and several millimeters in diameter.

Example 2

Figure 2:
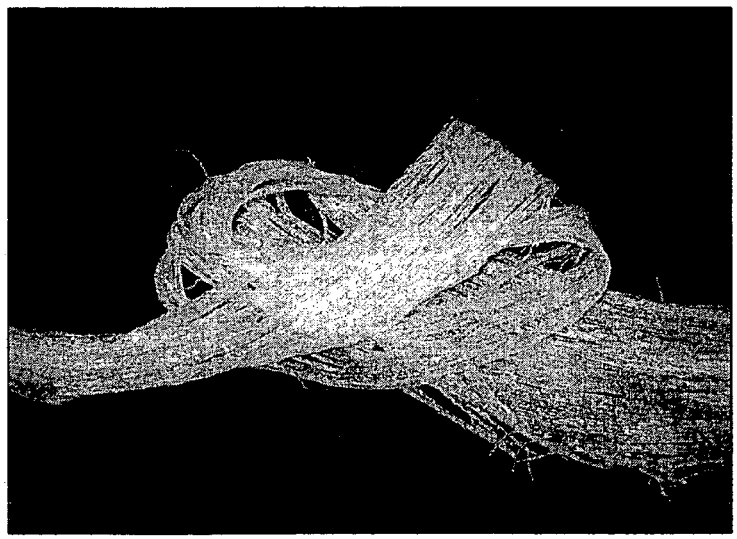
FIG. 2 shows another photographic depiction of an additional embodiment of novel silicone fibers according to the teachings of the present disclosure.
Figure 3:
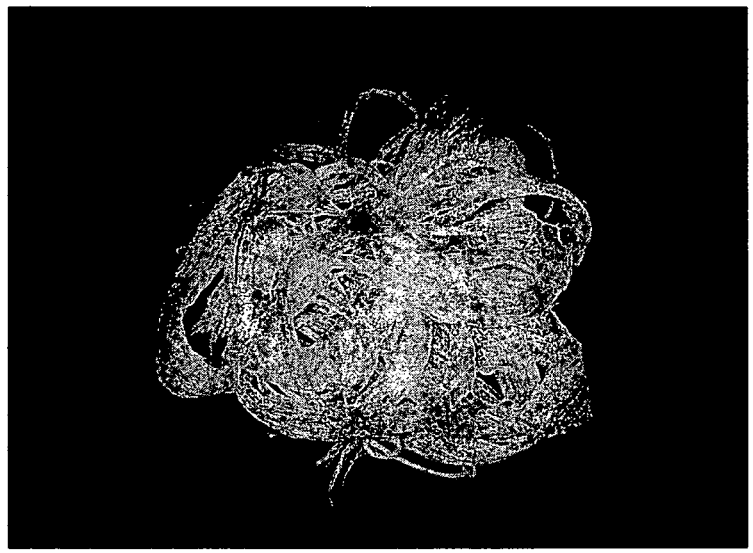
FIG. 3 likewise illustrates strands of novel silicone products according to the teachings of the present disclosure.

Referring now to FIG. 2 and FIG. 3, the process steps set forth above in the first example apply, however the diameters achieved are larger, here silicone fibers may be created also by mixing the silicone emulsion combining at least one of the ratios selected from the group consisting of 30/70, 40/60 and substantially equal aliquots of the two different liquid silicone precursors, of silicone A and B, medical grade (available also from Applied Silicone, Liquid Silicone Rubber, LSR 10, Part A, Lot 17689, and Silastic.RTM. Q7-4850 Lot hh 063161; Part B Silastic.RTM. Q7-48750 medical grade liquid silicone rubber). Medical grade silicone ingredients yield biocompatible product that may be used to fill containers used, for example for cosmetic facial enhancements, or as breast implants without any concerns about leakage, biocompatability, contamination, or many of the other problems which currently exist (see, for example FIGS. 8-10). The process steps are similar to Example I, and different from the prior art by using a metal die, which is in its most rudimentary form simply a metal disc with apertures extending through it, following at least about ten minutes of mechanical agitation which suspends air into the mixture.

Referring specifically now to FIG. 3, strands of silicone having a larger diameter may also be mixed from at least one of the Dow Corning® brand of constituents, intermediates from GE Silicones® or the Walker-Chemie® brands of products. The silicone filaments, fibers and strands have elastic memory, tensile strength and a sufficiently high fill density in a compacted state rendering them effective for occupying a predetermined space over time without degrading, the diameter of the objects of this example are greater than several millimeters in diameter.

Example 3

Figure 4:
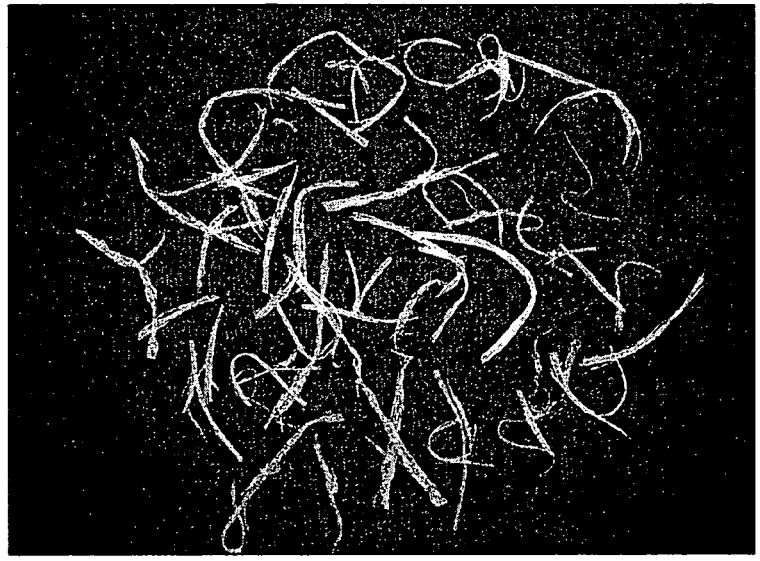
FIG. 4 is a photograph of pieces of novel silicone products according to teachings of the present invention.
Figure 5:
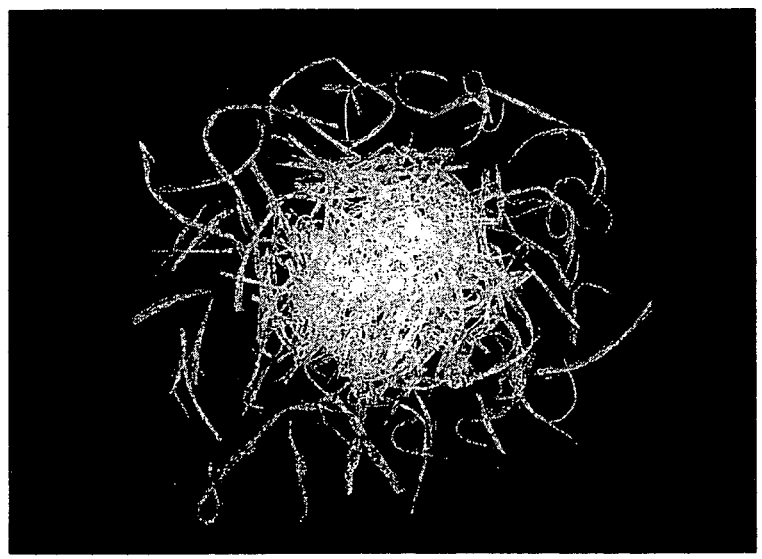
FIG. 5 photographically depicts finer pieces of novel silicone products, according to the disclosure.
Figure 6:
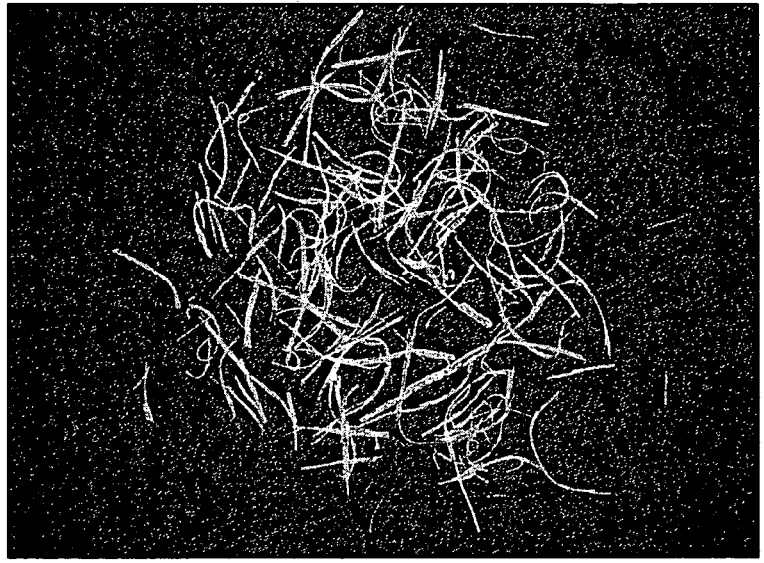
FIG. 6 is a photograph of pieces of twine according to the present novel silicone products of the present disclosure.

Referring now to FIG. 4 through FIG. 6, exemplary embodiments with varying diameters are shown, that have been subjected to additional chopping or cutting step during the finishing process.

As discussed above, a silicone emulsion was made by combining at least one of the ratios selected from the group consisting of 30/70, 40/60 and substantially equal aliquots of the two different liquid silicone precursors, substantially equal aliquots of silicones A and B, medical grade selected from the group consisting of 10, 20, 30, 40 and 50 type (manufacturer's suggestion for second-wise definitions of the optimal curing time for cross-linking to be achieved). The sources are as discussed in the first two examples. Mechanical agitations using a motor driven mixing machine were imparted to the mixture for approximately ten minutes.

The fluffed emulsion was then moved into a pressing machine having a die plate having a plurality of apertures through which it was extruded onto a rotating deposit plate into a drying chamber at 350° F. The resulting product was chopped into pieces, as shown in FIG. 4, FIG. 5, and FIG. 6, as discussed above, curtain-like strands may be extruded directly from the die plate into the drying chamber, for example, the curtain-like group of filaments is deposited directly on a metal mesh that prevents sticking and allows for easy removal. The metal mesh itself is mounted on a moving belt.

Example 4

Figure 7:
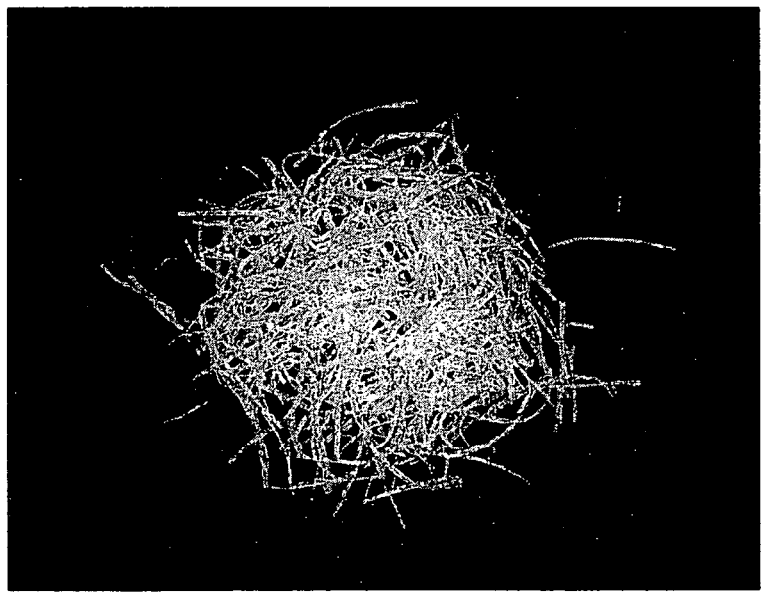
FIG. 7 depicts photographically yet a finer grade of twine according to the teachings of the present disclosure.

Referring now to FIG. 7, once again a silicone emulsion was made by combining substantially equal aliquots of silicones A and B, medical grade selected from the group consisting of 10, 20, 30, 40 and 50 type (manufacturer's suggestion for second-wise definitions of the optimal curing time for cross-linking to be achieved). (Rhodia-A LSR-4330 Silbione® HCA Part #V50131A-40 Lot 0409031, B LSR-10 Silbione®D HC Part #V500004B-40 Lot 26776, Medical Grade available as discussed above). Mechanical agitations using a motor driven mixing machine were impacted to the mixture for approximately ten minutes.

The fluffed emulsion was then moved into a pressing machine having a die plate having a plurality of apertures through which it was extended onto a rotating plate into a drying chamber at 350° F. By sending the extruded filaments onto a round rotating dish, these exemplary embodiments were dried in under a minute.

The silicone is extruded at the same speed as the rotations of the drying or receiving plate which provides enough time for drying prior to another layer of silicone being deposited.

Example 5

Figure 8:
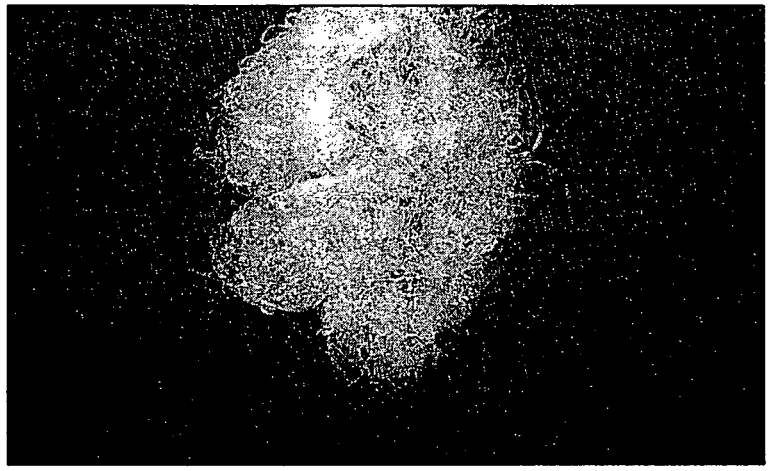
FIG. 8 photographically illustrates an embodiment of silicone thread, according to the teachings of the present disclosure.

Referring now to FIG. 8, a view is shown which photographically illustrates an embodiment of silicone thread, and by using smaller configuration of apertures, or a screen, a finer grade of filament is achieved. As in the above examples, a silicone emulsion was made by combining at least one of the ratios selected from the group consisting of 30/70, 40/60 and substantially equal aliquots of the two different liquid silicone precursors, substantially equal aliquots of silicones A and B, medical grade as discussed above.

Mechanical agitations using a motor driven mixing machine were impacted to the mixture for approximately ten minutes and then the fluffed emulsion was then moved into a pressing machine having a die plate having a plurality of apertures through which it was extended onto a rotating plate into a drying chamber at 350° F. By sending the extruded filaments onto a round rotating dish, these exemplary embodiments were dried in under a minute. The silicone was extruded at the same speed as the rotations of the drying or receiving plate which provided enough time for drying prior to another layer of silicone being deposited.

According to this example miniscule holes are located on the die plate or extrusion nozzles and as the silicone moves through the holes it forms strands which hang down in a curtain-like fashion. Finer threads are dried for shorter periods of time, and this range for this example is between roughly 1/3 and 2/3 of a minute, with a resulting novel aerated silicone filament defined by having at least one of a nano, pico, meso or millimeter scale longitudinally extended axis about a central plane defined by a cathetus.

Figure 9:
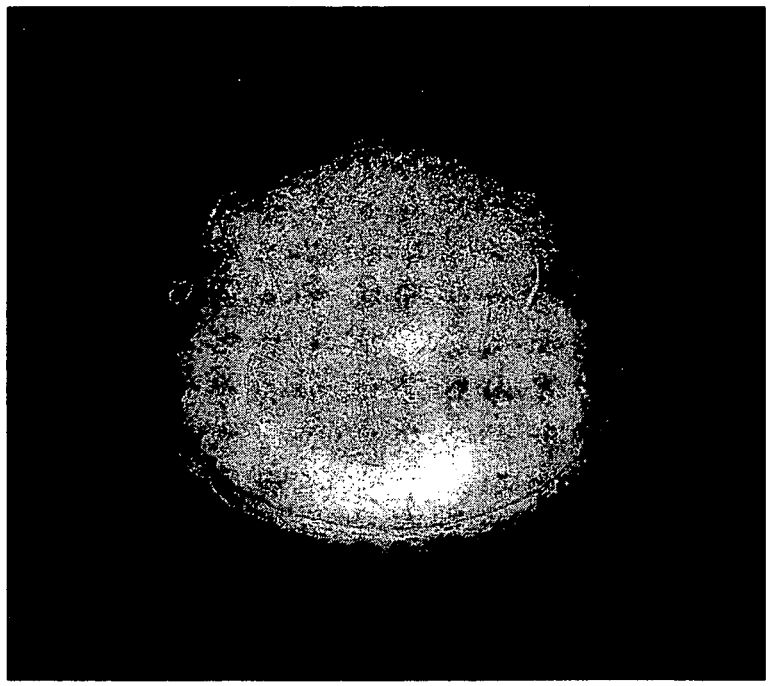
FIG. 9 shows an assembly including a silicone thread being packed into an exemplary holder for the same, according to embodiments of the teachings of the present disclosure.

FIG. 9 shows an assembly including a silicone thread being packed into an exemplary holder for the same, according to embodiments of the teachings of the present disclosure, those having a modicum of skill in the art will understand that both the container and the threads are biocompatible, and that none of the challenges of fluid filled media are present according to the teachings of the present invention.

Figure 10:
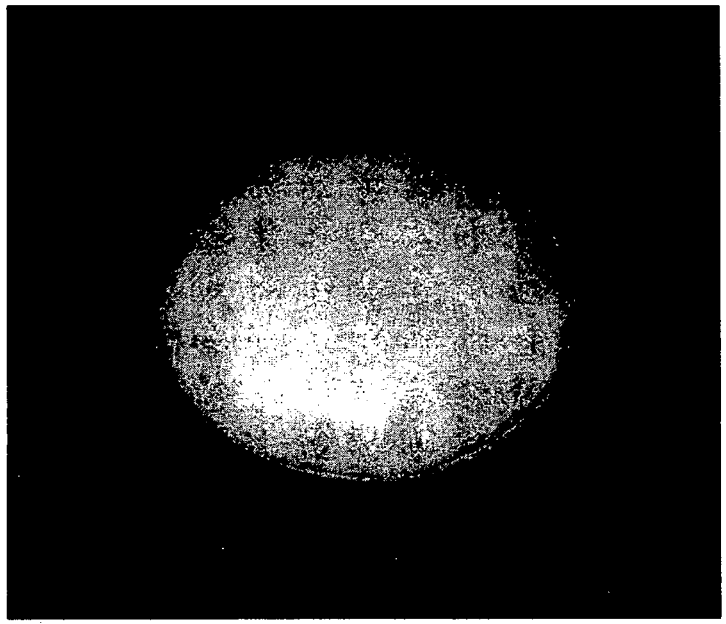
FIG. 10 is a photograph of an assembly using threads and an implantable exemplary prosthesis, according to teachings of the present disclosure.

FIG. 10 is a photograph of an assembly using threads and an implantable exemplary prosthesis such as one appropriate to use as a breast implant, according to teachings of the present disclosure. Those skilled in the art will appreciate that the threads of the instant teachings provide many design options and that they will work with, or in place of many aspects of conventional systems.

Figure 11:
FIG. 11 is a photograph of a thin sheet of silicone according to the present disclosure.
Figure 12:
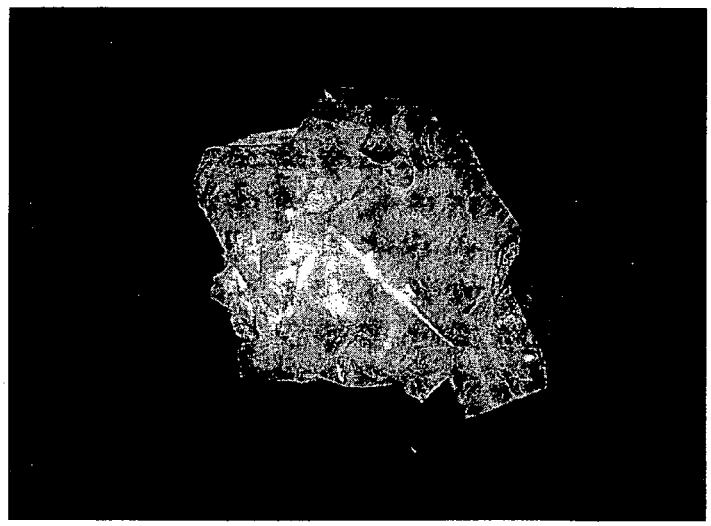
FIG. 12 shows an alternate ribbon like film of novel silicone according to the teachings of the present disclosure.

Referring now to FIG. 11 and FIG. 12 there are shown photographs of thin sheets of silicone according to the present disclosure, and an alternate ribbon like film of novel silicone according to the teachings of the present disclosure. These products are generated by processes similar to the example described above, as modified by the details according to the process in FIG. 18 and its many sub-parts. Likewise, variations of the processes taught herein, such as, spreading a thin film of silicone emulsion onto a heating plate is done, as when one makes an omelette or crepe, and depending upon the thickness, the film-like construction cures extremely fast, in a matter of seconds.

Figure 13:
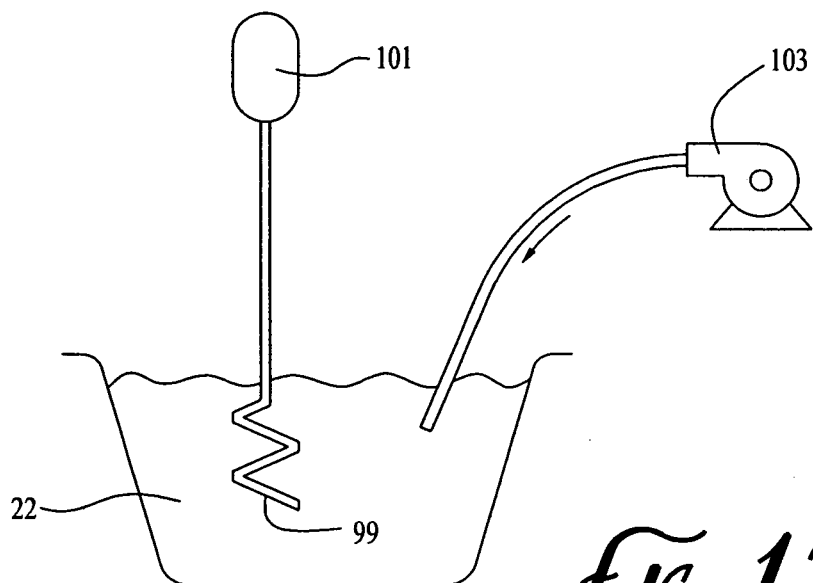
FIG. 13 shows an assembly used according to a process for making the instant disclosure.

Referring now to FIG. 13 there is shown an assembly used according to a process for making the instant disclosure, illustrated in schematic form. Those skilled in the art will understand that motor 101 (for example available from B&B Motoro & Control Corp. of 96 Spring Street, N.Y., N.Y. 10012/Bodine Electric Company, 115 V, 60 HZ Model Number 728D2202/Type KCI-24A2) represents any conventional mixing mechanism connected to a blade or stirring arm or means 99 effective to stir, or mechanically agitate the mixture 22 of silicone emulsion was made by combining substantially equal aliquots of silicones A and B, medical grade as referenced above.

Air source 103 allows the mixture to have a grease-like viscosity by imparting aeration to the emulsion, as likewise would be understood by those having a modicum of skill in the art. At least about 10 minutes of mixing time is effective for use with the teachings of the present invention as discussed in the examples which are set forth above, and the claims defined below.

Figure 14:
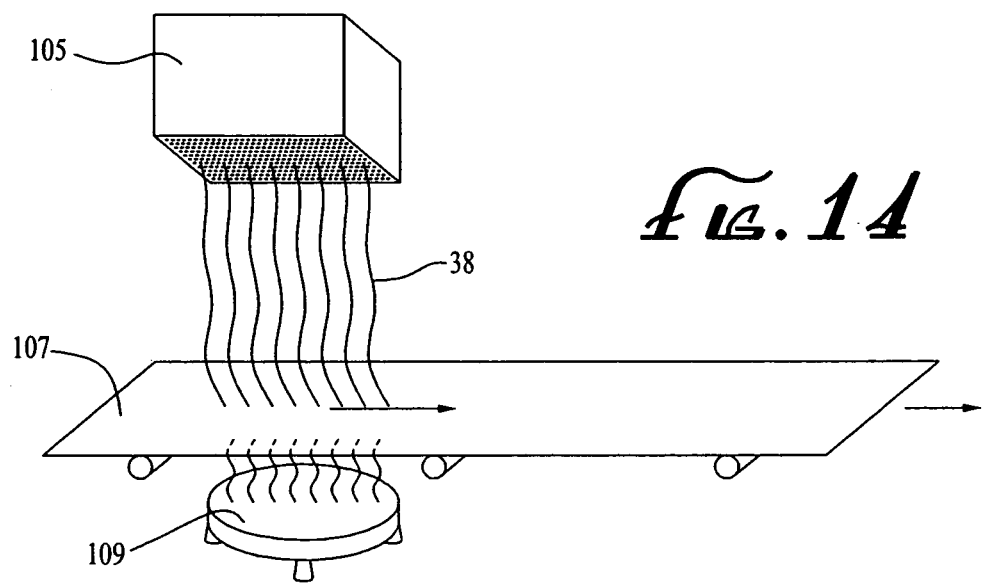
FIG. 14 shows an assembly used according to a process for making the instant disclosure.

FIG. 14 further shows an assembly used according to a process for making the instant disclosure, whereby the steps of pressing the fluffed emulsion 22 through a pressing machine 105 equipped with a die plate, extruding silicone filaments 38 onto a belt 107 (likewise a plate or dish, not shown works), and drying the silicone filaments using a heat source 109 is done.

FIG. 15 shows another assembly used according to a process for making the instant disclosure whereby dual agitator motor assembly 102 (for example, including a 20 RPM motor at a top position, in communication with two 100 RPM motors, one with a clockwise rotation, and the other with a counterclockwise rotation) uses conventional mixing mechanisms connected to at least two blades or stirring arms 99 effective to stir, or mechanically agitate the mixture 22 of silicone emulsion was made by combining substantially equal aliquots of silicones A and B, medical grade as referenced above.

Air source 103 is connected with tubing for injection of air into the mixture, and allows the mixture to have a viscous paste-like consistency by imparting aeration to the emulsion, as likewise would be understood by those having a modicum of skill in the art. At least about 10 minutes of mixing time is effective for use with the teachings of the present invention as discussed in the examples which are set forth above, and the claims defined below. Output can be taken through port 17, which may have conventional doors, valves or gating means associated therewith a would be known to those skilled in the art.

Referring now to FIG. 16, output from port 17 of FIG. 15 may pass into 119, 125 as it is a sliding device using piston 122 to drive emulsion 22 (not shown) by way of reversible motor 115 driving shaft with center piece 117 back an forth, to leverage outputs 121 and 127 onto plate 129, which carries a row of tiny holes.

FIG. 17 likewise picks up the exudate 38 and mechanically brings it through a drying chamber 111 at 350 degrees Fahrenheit, using heat source 109 and metallic wire mesh 113. Filaments, fibers, strands 110 are thus dried for between 30 seconds and one and one-half minutes.

FIG. 18 A through H each shows one step in an alternate process used according to the method for making the instant disclosure, as will be clear to those skilled in the art, having read the above specification and studied the claims appended hereto. Not unlike the process disclosed in U.S. Pat. Nos. 6,612,823 and 6,585,504 each of which are expressly incorporated herein by reference as if fully set forth herein.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A composition comprising aerated silicone filaments, said aerated silicone filaments comprising a compound having a first silicone rubber (A) and a second silicone rubber (B), the first silicone rubber comprising dimethyl methylvinyl siloxane and the second silicone rubber comprising dimethyl methylhydrogen siloxane,
    wherein the aerated silicone filaments have elastic memory, and tensile strength, wherein the composition is generated by a process for generating novel silicone constructions, comprising, in combination, the steps of:
    providing predetermined aliquots of two different liquid silicone rubbers A and B; combining at least one ratio selected from the group consisting of 30/70, 40/60 and substantially equal measurements of the respective aliquots of the two different liquid silicone rubbers; adding air to the combinant silicone mixture; mixing the resulting silicone emulsion to create a fluffed emulsion; and finishing the process to create a desired end product, and wherein the finishing step further comprises:
    pressing the fluffed emulsion through a pressing machine equipped with at least one of a wire mesh screen assembly and a die plate; extruding silicone filaments onto a receiving plate; and, drying the silicone filaments inside of a heating chamber.

2. The composition of claim 1, wherein the ratio of (A)/(B) is 30/70.

3. The composition of claim 1, wherein the ratio of (A)/(B) is 40/60.

4. The composition of claim 1, wherein the ratio of (A)/(B) is substantially equal.

5. The composition of claim 1, wherein the aerated silicone filaments are configured as ribbon shaped filaments.

* * * * *